United States Patent [19]

Arpino

[11] Patent Number: 4,922,338
[45] Date of Patent: May 1, 1990

[54] LINE-OF-SIGHT INSPECTION SYSTEM

[76] Inventor: Ronald G. Arpino, 25 Damien Rd., Branford, Conn. 06405

[21] Appl. No.: 317,751

[22] Filed: Mar. 2, 1989

[51] Int. Cl.⁵ .............................................. H04N 7/18
[52] U.S. Cl. ..................................... 358/106; 358/93
[58] Field of Search .......................... 358/106, 93, 241

[56] References Cited

U.S. PATENT DOCUMENTS 4,266,223  5/1981  Frame ................................. 358/241
4,786,154  11/1988  Fantone ................................ 358/93

Primary Examiner—Howard W. Britton
Attorney, Agent, or Firm—John H. Crozier

[57] ABSTRACT

An inspection system in which the image viewed and the object being inspected lie in a single line of sight of the inspector. In one preferred embodiment, the inspector views a first side of back-to-back mirrors disposed at a 45 degree angle to the line of sight of the inspector. A video camera is disposed to view the reflection of the object from the second side of the mirrors and the image on a CRT is reflected from the first side of the mirrors. Thus, the image seen by the inspector is correctly spacially oriented with respect to the object and the inspector may manually position or re-position the object as easily as if the inspector were directly viewing it. In another preferred embodiment, a flat screen CRT and a miniature video camera are aligned in the direct line of sight from the inspector to the object. Zoom and crosshair features may be provided in either embodiment.

9 Claims, 2 Drawing Sheets

LINE-OF-SIGHT INSPECTION SYSTEM

BACKGROUND OF THE INVENTION

1. Field of the Invention

The present invention relates to inspection systems generally and, more particularly, to a novel inspection system in which an image of the item being inspected and the item itself lie in a single line of sight of the inspector.

2. Background Art

Various types of inspection system are widely used in a broad range of applications. Typically, such systems are employed in the manual or semi-automatic inspection of finished or in-process manufactured items and usually require the inspector to manually place one such item after another in the field of view of a video camera. Frequently, it is necessary to view magnified portions of the items.

Prior known systems which employ video images in an inspection system are described, for example, in U.S. Pat. Nos. 3,818,125, issued June 18, 1974, Ito Butterfield and 4,232,335, issued Nov. 4, 1980, to Nakagawa et al. The former patent discloses a stereo television microscope in which the operator views a cathode ray tube (CRT) which is disposed at an angle from what would be the line of sight from the operator to the object being viewed. The latter patent discloses a numerical control tape preparation machine which includes a horizontal surface on which a printed circuit board may be placed, a video camera mounted vertically over the board, and a CRT monitor screen mounted in a vertical surface at one side of the camera.

A substantial disadvantage with such arrangements is that when the operator needs to place, or readjust the placement of, the object to be viewed, the operator experiences spacial disorientation, since the object the operator is manipulating is in one line of sight, while the image he is viewing is in another line of sight. This arrangement makes it difficult to quickly place the object in the proper position to be viewed and can result in a certain amount of frustration and fatigue of the inspector, as well as inefficiency caused by the amount of time required for placing, or readjusting the placement of, the object. It would thus be desirable to employ an inspection system in which the object and the image being viewed are in a single line of sight.

Accordingly, it is a principal object of the present invention to provide an inspection system which provides correct spacial orientation.

It is another object of the invention to provide such a system that is simply constructed and flexible in application.

Other objects of the invention, as well as particular features and advantages thereof, will, in part, be obvious and will, in part, be apparent from the following description and the accompanying drawing figures.

SUMMARY OF THE INVENTION

The present invention accomplishes the above objects, among others, by providing an inspection system in which the image viewed and the object being inspected lie in a single line of sight of the inspector. In one preferred embodiment, the inspector views a first side of back-to-back mirrors disposed at a 45 degree angle to the line of sight of the inspector. A video camera is disposed to view the reflection of the object from the second side of the mirrors and the image on a CRT is reflected from the first side of the mirrors. Thus, the image seen by the inspector is correctly spacially oriented with respect to the object and the inspector may manually position or re-position the object as easily as if the inspector were directly viewing it. In another preferred embodiment, a flat screen CRT and a miniature video camera are aligned in the direct line of sight from the inspector to the object. Zoom and cross-hair features may be provided in either embodiment.

DETAILED DESCRIPTION OF THE PREFERRED EMBODIMENTS

Figure 1:
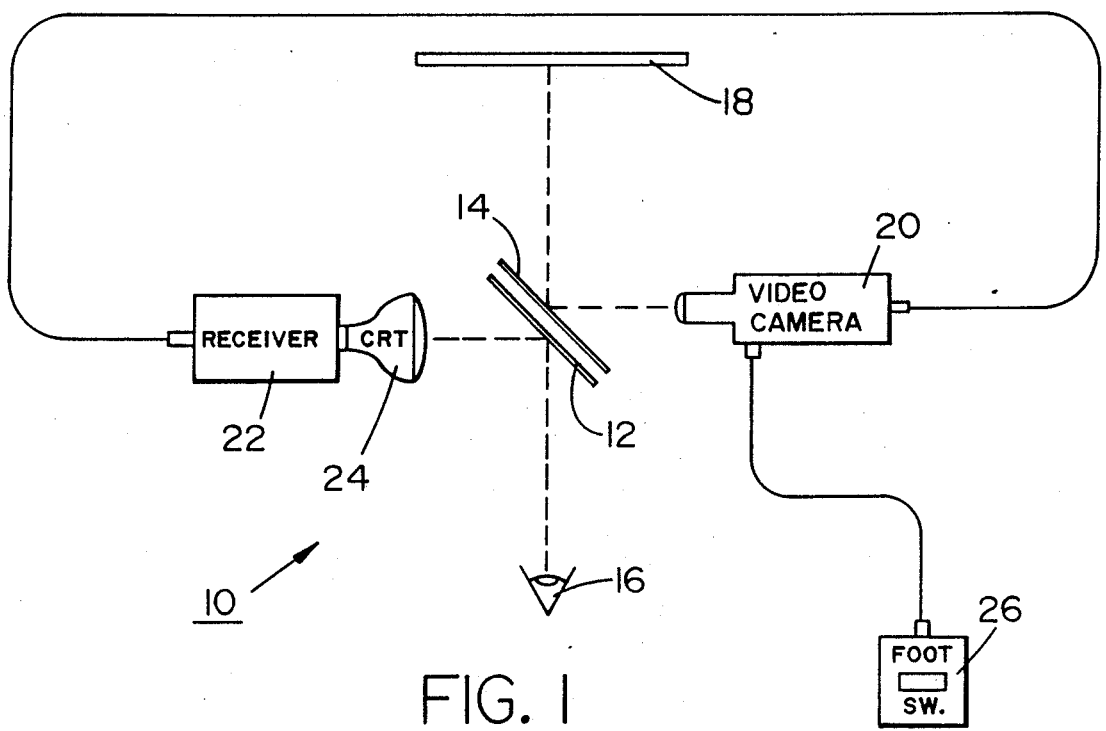
FIG. 1 is a schematic representation of one embodiment of the inspection system of the present invention.

Referring now to the Drawing, in which identical elements are given the same reference numerals throughout the various figures, FIG. 1 shows schematically one embodiment of the inspection system of the present invention, generally indicated by the reference numeral 10. System 10 includes two mirrors 12 and 14 which are disposed in back-to-back relationship at a 45 degree angle to the line of sight between the eye 16 of the inspector and an object 18 which is being inspected. A video camera 20 is disposed at a 45 degree angle with respect to the plane of mirror 14 so as to view the reflected image of object 18. The video signal produced by video camera 20 is received by video receiver 22 which causes an image of object 18 to be displayed on a CRT 24. CRT 24 is disposed at a 45 degree angle with respect to mirror 12 so that the image on the CRT is reflected from the mirror to the inspector's eye 16. Video camera 20 is preferably of the type employing a zoom lens which may be controlled by a switch 26 which is preferably a foot switch. Although a hand operated switch may be employed, the use of a foot switch allows the inspector to use both hands in holding or placing object 18.

It can be seen from inspection of FIG. 1 that, with the arrangement of the elements of inspection system 10, the inspector's eye 16 "sees" object 18 as if mirrors 12 and 14 were not in the line of sight of the inspector.

Figure 2:
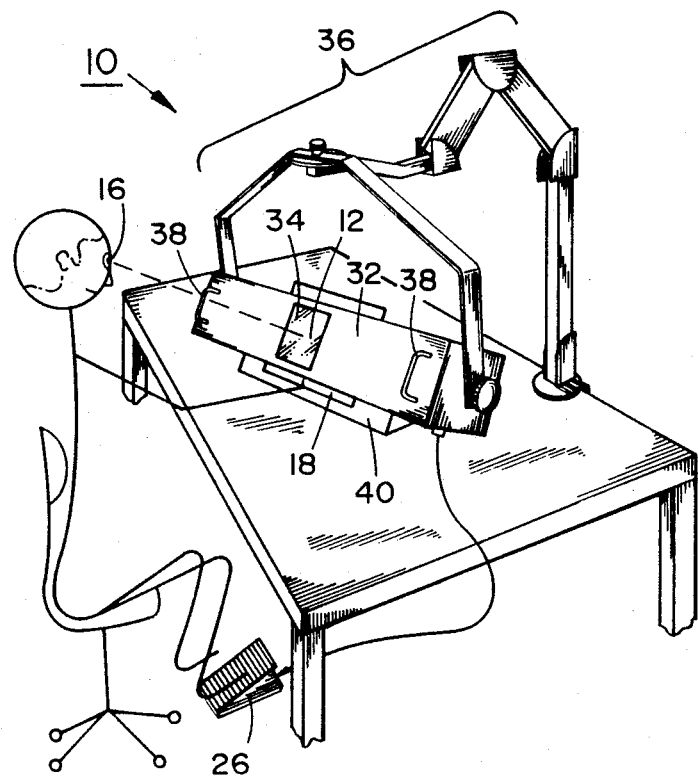
FIG. 2 is a perspective view of the system of FIG. 1 in use.

FIG. 2 is a perspective view of inspection system 10 wherein mirror 14, video camera 20, video receiver 22 and CRT 24 (all not visible) are disposed within a housing 32. Mirror 12 is visible within housing 32 through a port 34. Housing 32 is movably supported by an articulated support 36 and has handles 38 for convenient positioning of the housing. A focusing plane 40 is provided so that object 18 may be easily and quickly placed at the proper distance from housing 32. Video camera 20 may also be provided with an autofocus feature if desired.

It is preferred that housing 32, in the configuration shown, have a minimum practical vertical dimension, so that there is minimum vertical separation between the image on first mirror 12 and the direct image of object 18, as seen by the inspector, to assist the inspector in orienting the object. It is also desirable that the thickness of housing 32 be at a minimum, so that object 18 may be as close as possible to the inspector.

Figure 3:
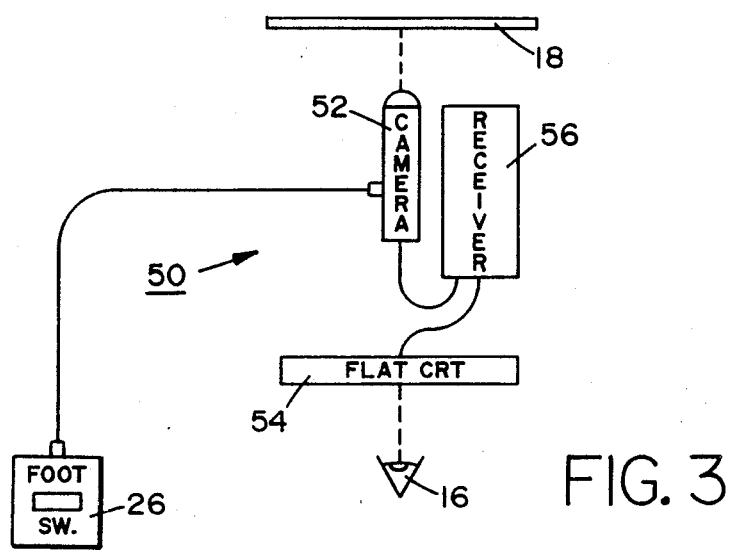
FIG. 3 is a schematic representation of another embodiment of the inspection system of the present invention.

FIG. 3 schematically illustrates another embodiment of the inspection system of the present invention, generally indicated by the reference numeral 50. Inspection system 50 employs no mirrors, but instead has a miniature video camera 52 and a flat screen CRT 54 all directly in the line of sight between inspector's eye 16 and object 18. A video receiver 56 and zoom switch 26 complete the operating elements of inspection system 50. Inspection system 50 may be mounted in any suitable housing (not shown) which may desirably have length and height dimensions not greatly exceeding the dimensions of flat screen CRT 54, thus permitting as much as possible of object 18 to be seen by the inspector to aid in placing or readjusting the object.

It is within the intent of the present invention to alternatively employ a solid-state camera for element 52 and/or an LCD screen or plasma screen for element 54.

Figure 4:
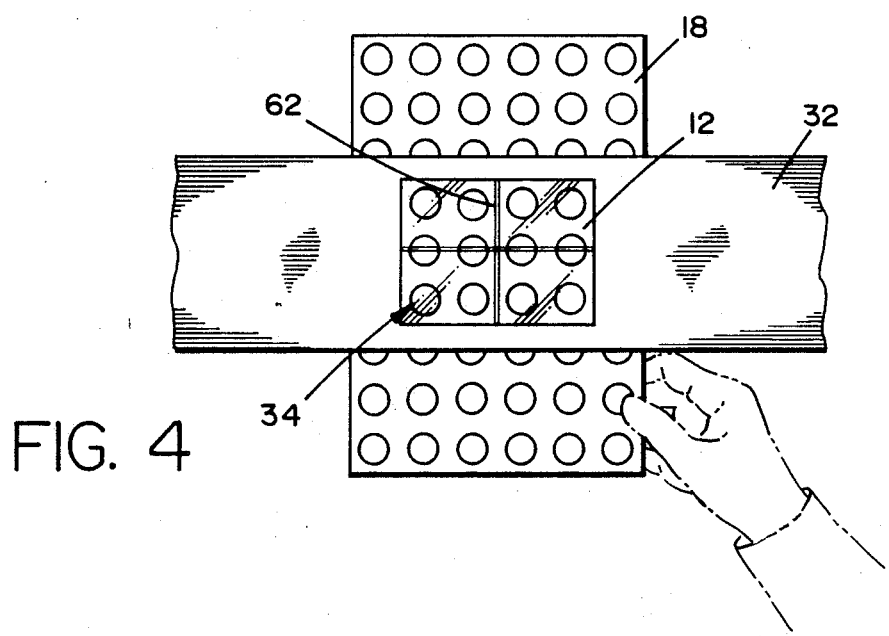
FIG. 4 illustrates an unmagnified image of an object being inspected as seen by an inspector using the present invention.

FIG. 4 shows a portion of inspection system 10 of FIG. 2 as seen by the inspector with no magnification of object 18. Here, for illustrative purposes, object 18 is shown as having a plurality of equally spaced holes, as at 60. It can be seen that the image of the portion of object 18 reflected in mirror 12 is correctly spacially oriented with the actual position of the object. Cross hairs, as at 62, may be provided to assist in pinpointing certain features on object 18 to be magnified.

Figure 5:
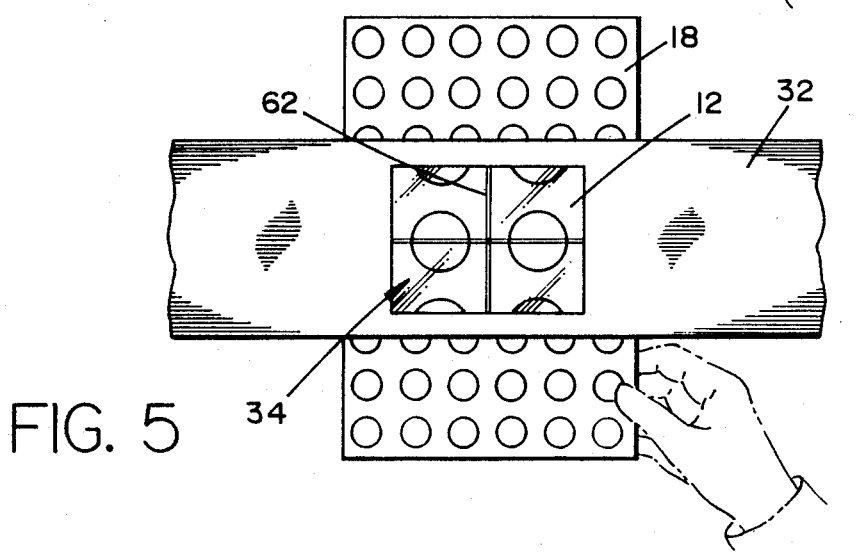
FIG. 5 illustrates a magnified image of a portion of an object being inspected as seen by an inspector using the present invention.

FIG. 5 shows the arrangement of FIG. 4 with a portion of the image of object 18 magnified. It may be assumed that the inspector seeing the view of FIG. 4 found some feature of object 18 that warranted closer inspection and the inspector operated zoom switch 26 to enlarge that feature. It is here that cross hairs 62 are especially useful, as the inspector can assure that the area of interest is kept centered in the field of view as the image is magnified.

The electronic components of systems 10 and 50 are conventional in the art and mirrors 12 and 14 are preferably first-surface mirrors so that the reflected images will be as true as possible. The system is simply and economically assembled and easy to use, being self-contained and requiring no set-up procedure to initiate inspection. The only adjustments required during use are the positioning of the system with respect to whatever is being inspected, if necessary, and operation of a zoom switch.

With the inspection information embodied in a video signal, the information may be viewed at other locations, for example by an inspection supervisor. Also, the signal may be digitized and the digital information stored, printed, or otherwise processed.

From the above, it will be understood that what has been disclosed is a unique line-of-sight video inspection system in which the image of the object viewed and the object are correctly spacially oriented. With such a system, an inspector can easily and quickly position, or re-position an object, identify a certain area of interest, and cause the image of that area to be magnified—all while looking toward the object.

It will thus be seen that the objects set forth above, among those made apparent from the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. An inspection system for inspection of an object by an inspector, comprising:
   (a) display means disposed in the line of sight between said inspector and said object; and
   (b) image processing means to selectively cause either:
      (i) an unmagnified image of at least a portion of said object to be displayed on said display means, such that said image and said at least said portion of said object are correctly spacially oriented with respect to said line of sight; or
      (ii) a magnified image of part of said at least a portion of said object to be displayed on said display means, such that said magnified image of part of said at least a portion of said object is corectly spacially oriented with respect to said line of sight.

2. An inspection system, as defined in claim 1, where said image processing means comprises video means to provide a video signal representative of an image of said at least said portion of said object.

3. An inspection system, as defined in claim 2, wherein said means to display said image comprises a CRT disposed in the line of sight between said inspector and said object.

4. An inspection system, as defined in claim 2, wherein said means to display said image comprises an LCD screen disposed in the line of sight between said inspector and said object.

5. An inspection system, as defined in claim 2, wherein said means to display said image comprises a plasma screen disposed in the line of sight between said inspector and said object.

6. An inspection system, as defined in claim 2, wherein said image processing means further comprises:
   (a) a CRT;
   (b) a video receiver to receive said video signal and produce said image on said CRT; and
   (c) a first mirror disposed in said line of sight and at a 45 degree angle with respect to both said line of sight and with respect to said CRT.

7. An inspection system, as defined in claim 6, further comprising:
   (a) a second mirror disposed at a 45 degree angle with respect to said object;
   (b) said video means comprises a video camera disposed at a 45 degree angle with respect to said second mirror such that said image is the reflection of said at least said portion of said object from said second mirror.

8. An inspection system, as defined in claim 7, wherein said video camera includes a zoom lens.

9. An inspection system, as defined in claim 8, wherein said zoom lens is activated by a foot switch.

* * * * *